United States Patent [19]

Volk

[11] Patent Number: 4,738,521
[45] Date of Patent: Apr. 19, 1988

[54] LENS FOR INDIRECT OPHTHALMOSCOPY

[76] Inventor: David Volk, 3336 Kersdale Rd., Pepper Pike, Ohio 44124

[21] Appl. No.: 437,279

[22] Filed: Oct. 28, 1982

[51] Int. Cl.$^4$ ............................................... A61B 3/10
[52] U.S. Cl. ..................................... 351/205; 350/432
[58] Field of Search ................. 351/205; 350/432, 435

[56] References Cited

U.S. PATENT DOCUMENTS 4,469,413 9/1984 Shirayanagi ...................... 350/432

FOREIGN PATENT DOCUMENTS 127510 10/1980 Japan .................................. 350/432

Primary Examiner—Rodney B. Bovernick
Attorney, Agent, or Firm—Baldwin, Egan, Hudak & Fetzer

[57] ABSTRACT

A lens for use in indirect ophthalmoscopy having two functions; firstly as a condensing lens converging light from an ophthalmoscope light source to the pupil of the eye and thereby illuminating the fundus of the eye, and secondly and simultaneously as an image forming lens which forms an aerial image of the fundus of the eye, which image is viewed monocularly with a monocular indirect ophthalmoscope or binocularly and stereoscopically with a binocular indirect ophthalmoscope. The novel features of the lens of this invention are that both the front and back surfaces of the lens are positive aspheric surfaces of revolution of conoid type on a common axis of revolution, the dioptric power at the apex of the front surface of the lens being approximately twice that of the apex of back surface of the lens, which back surface faces the eye being examined, the eccentricity of the front surface bearing a definite relationship to the eccentricity of the back surface, the eccentricities of the two surfaces of the lens being a function of the sum of the dioptric powers of the two surfaces of the lens, the eccentricities and apical dioptric powers of the surfaces of the lens being such that the lens converges the light from the ophthalmoscope light source to a precise image of the source at the entrance pupil of the eye, and simultaneously the lens forms with the light emerging from the eye a substantially flat aerial image of the fundus of the eye in which images the aberrations of the image including curvature, astigmatism and distortion are optimally corrected.

8 Claims, 6 Drawing Sheets

LENS FOR INDIRECT OPHTHALMOSCOPY

This invention relates to an improvement in an optical lens for indirect ophthalmoscopy, which has two functions: firstly as a condensing lens converging light from an ophthalmoscope light source to the entrance pupil of the eye and thereby illuminating the fundus of the eye, and secondly and simultaneously, utilizing the light emerging from the eye, as an image forming lens which forms an aerial image of the fundus of the eye, which image is viewed monocularly with a monocular indirect ophthalmoscope or binocularly and stereoscopically with a binocular indirect ophthalmoscope. The novel features of the lens of this invention are that both the front and back surfaces of the lens are positive aspheric surfaces of revolution of conoid type on a common axis of revolution, the dioptric power at the apex of the front surface of the lens being approximately twice that at the apex of the back surface of the lens, which back surface faces the eye being examined, the eccentricity of the front surface bearing a definite relationship to the eccentricity of the back surface, the eccentricities of the two surfaces of the lens being a function of the sum of the dioptric powers of the apices of the two surfaces of the lens, the eccentricities and apical dioptric powers of the surfaces of the lens being such that light from the lens converges the light from the ophthalmoscope light source to a precise image of the source at the entrance pupil of the eye, and simultaneously the lens forms with the light emerging from the eye a substantially flat aerial image of the fundus of the eye in which the aberrations of the image including curvature, astigmatism and distortion are optimally corrected. As is well known, the term eccentricity is a mathematical expression in which eccentricity is defined as the ratio existing between the distance from any point on a curve of a conic section to the focus and to the directrix.

BACKGROUND OF THE INVENTION

Sudarsky and Volk, in a paper entitled "Aspherical Objective Lenses As an Aid in Indirect Ophthalmoscopy, A Preliminary Report," reported on their investigation of existing conoid lenses designed for subnormal vision when used as condensing lenses for indirect ophthalmoscopy. As a result of their investigation they recommended the use of three powers of conoid lenses for use in indirect ophthalmoscopy, the 15, 20, and 30 diopter lenses, each of the lenses having one aspheric surface, the other surface being plano or spherical. In use, the front aspherical surface faces the examiner.

In about 1969, Nikon of Japan introduced aspheric lenses for indirect ophthalmoscopy, with the front surface aspherical and the back surface spherical.

Other Japanese manufacturers, including Kowa and Topcon, introduced their aspheric lenses for indirect ophthalmoscopy late in the 1970 decade. These lenses likewise had an aspherical front surface and a spherical back surface. In the United States of America, American Optical Company and Younger Lens Company also manufactured and sold indirect ophthalmoscopy lenses with one surface aspherical and the opposite surface spherical.

Recently Zeiss of Germany introduced their indirect ophthalmoscopy lens with one surface aspherical and the opposite surface spherical.

In all of the above prior art indirect ophthalmoscopy lenses, only one of the two surfaces is aspheric. Although such aspherical indirect ophthalmoscopy lenses are a great improvement over spherical indirect ophthalmoscopy lenses, lens aberrations still remain so that as a condensing lens the light from the ophthalmoscope light source is not converged to a sharply defined image at the entrance pupil of the eye, and as an image forming lens, the aerial image of the fundus is curved away from the examiner and is increasingly astigmatic peripheralward.

BRIEF DESCRIPTION OF THE PRESENT INVENTION

In the novel indirect ophthalmoscopy lens of this invention, both surfaces are positive conicoids of revolution on a common axis. The dioptric power at the apex of the back surface is approximately one-half that of the dioptric power at the apex of the front surface. The nominal dioptric power of any indirect ophthalmoscopy lens of this invention is the sum of the apical dioptric powers of the front and back surfaces of the lens; for example the dioptric power at the apex of the front surface may be 10 diopters and at the apex of the back surface 5 diopters or 9 and 4.5 diapters respectively, and the nominal power is 15 diopters. A lens of this invention may have a nominal dioptric power within the range of from 15 diopters to 50 diopters.

The diameter of an indirect ophthalmoscopy lens is generally some value between 52 mm and 31 mm, the lower power lenses having the larger diameters. In Table I, column I,

TABLE I

| Diopter | Large Lenses (MM) | Small Lenses (MM) |
| --- | --- | --- |
| 10 | 52 | 38 |
| 20 | 49 | 37 |
| 25 | 46 | 36 |
| 30 | 43 | 35 |
| 35 | 40 | 34 |
| 40 | 37 | 33 |
| 45 | 34 | 32 |
| 50 | 31 | 31 |
| 55 | 31 | 31 |

I have listed several lens powers within the range of 10 to 55 diopters, and in column 2 suggested lens diameters in millimeters which may be considered larger diameter indirect ophthalmoscopy lenses, and in column 3 of said table I have listed for the same lens powers suggested diameters in millimeters which may be considered small indirect ophthalmoscopy lenses. Generally a lens of 31 mm is quite satisfactory for the 50 and 55 diopter lens, and I have therefore suggested only a single diameter for these lenses, although a dimeter other than 31 mm may be utilized.

DETAILED DESCRIPTION OF INVENTION

Figure 1:
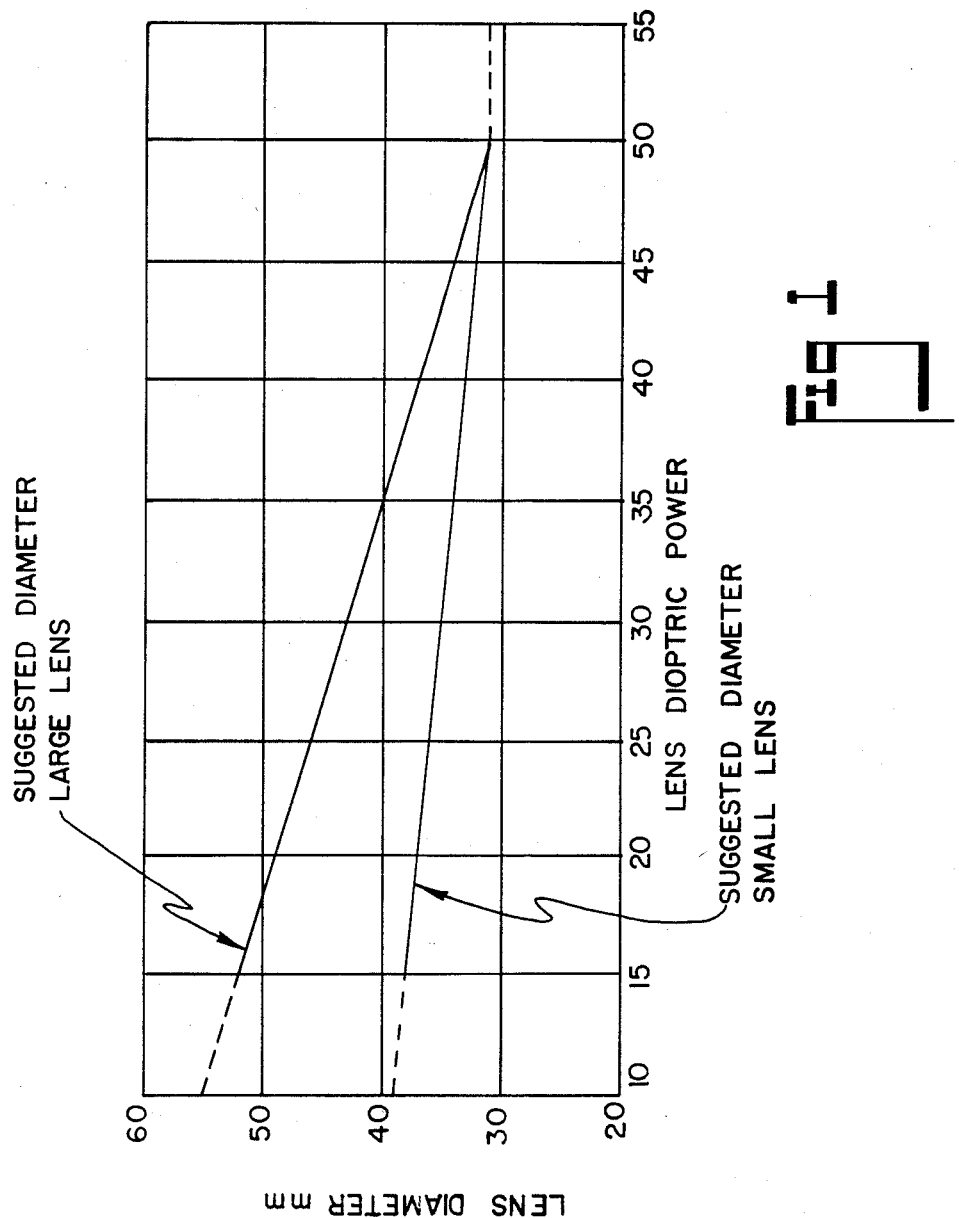
FIG. 1 is a graph of nominal dioptric power versus suggested diameters in millimeters of lenses incorporating the present invention.

Referring now to FIG. 1, a graph is illustrated of nominal dioptric power versus diameter in millimeters of indirect ophthalmoscopy lenses. The upper curve in the graph represents at any given point a suggested diameter for the lens power represented by that point, for lenses which may be termed large lenses. The lower curve in FIG. 1 is that for lenses which may be termed small indirect ophthalmoscopy lenses. FIG. 1 is only suggestive and lenses of diameters intermediate between the two curves, or larger or smaller than those represented by the upper and lower curves respectively can be utilized. The dotted line portions of FIG. 1 represent useful lenses with powers and associated diameters which are also considered as being within the scope of this invention, while the continuous line portions represent those lenses with preferred power and associated diameters. Lens powers between 10 and 15 diopters may be utilized when extreme magnification in the aerial image is desired while lens powers between 50 and 55 diopters may be utilized to increase the amount of fundus included in the aerial image.

Figure 2:
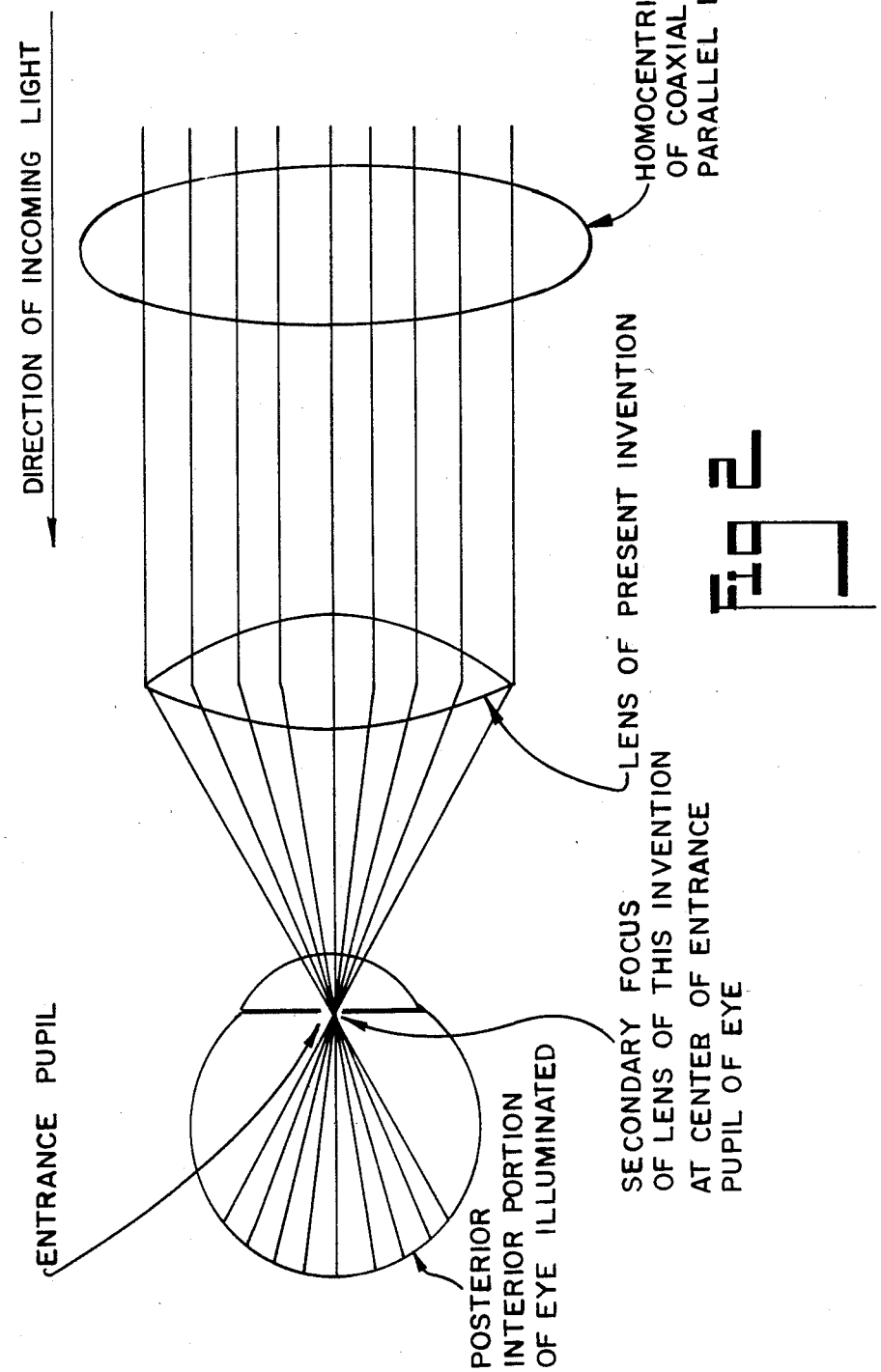
FIG. 2 is a schematic illustration of the eye and a lens of the present invention combined to form a telecentric system.
Figure 3:
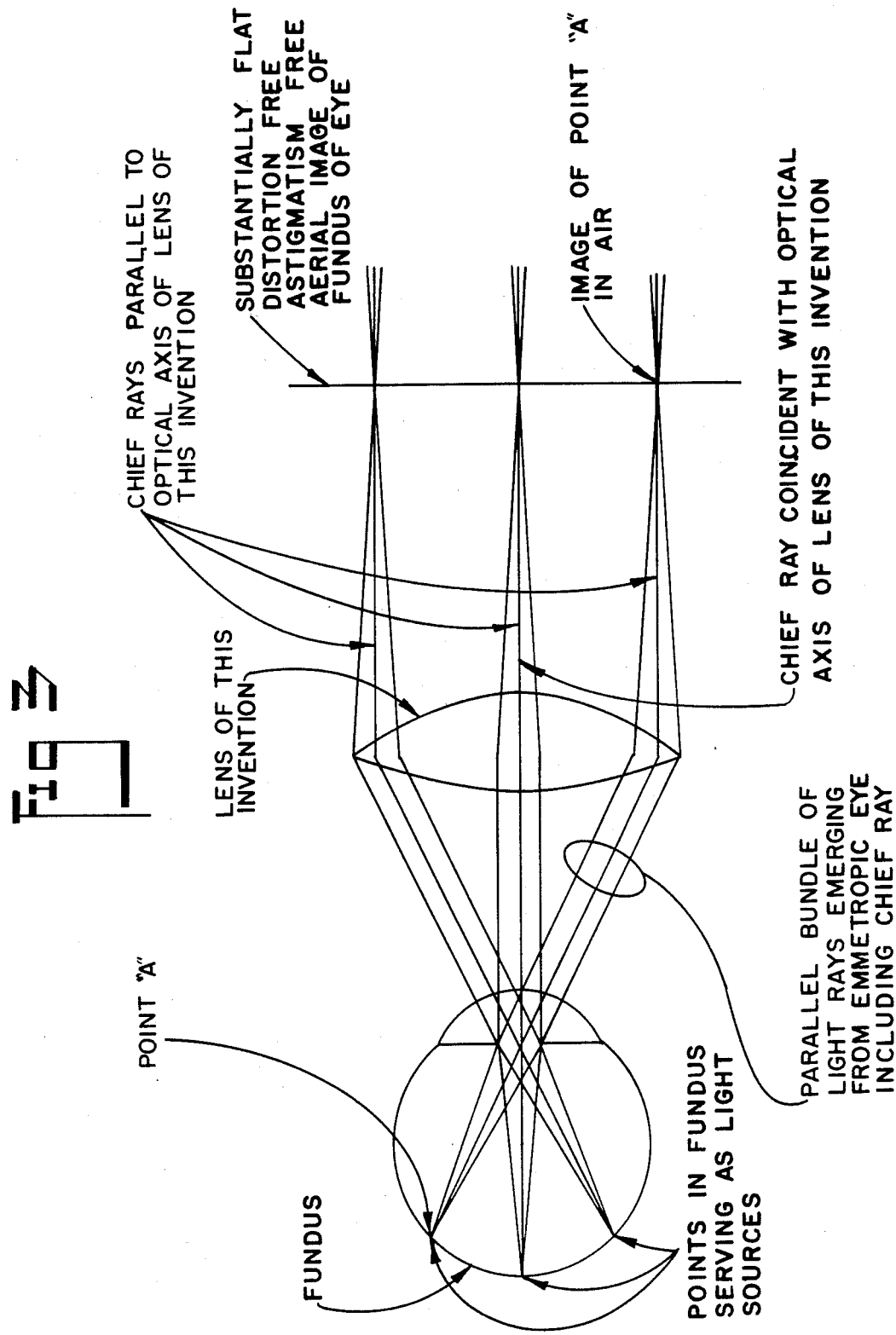
FIG. 3 is a schematic sketch illustrating the formation of an aerial image of the fundus with the eye and the lens of this invention combined as a telecentric system.

A first feature of the design philosophy which I have utilized as a basis in the design of the novel lens of this invention is that the lens and the eye form a telecentric system as shown in FIG. 2 wherein the secondary focus of the lens is at the center of the entrance pupil of the eye. Thus a homocentric bundle of coaxial and parallel light rays incident upon the front surface of the lens will be converged or condensed to a single point at the secondary focus of the lens which falls at the center of the entrance pupil of the eye. FIG. 2 is illustrative of the telecentric lens-eye combination just described, with the light rays proceeding beyond the pupil to illuminate the posterior portion of the interior of the eye. Simultaneously each illuminated point at the back of the interior of the eye sends out light in all directions, with homocentric bundles of light rays passing through the pupil of the eye. Assuming that the eye is a perfectly emmetropic eye, each bundle of light rays emerging from the eye will be a parallel bundle of light rays with the chief ray of each bundle passing through the center of the entrance pupil of the eye to be incident upon the indirect ophthalmoscopy lens as shown in FIG. 3 and then refracted by the lens to proceed parallel to the axis of the lens. A second feature of the design philosophy of the lens of this invention is that the indirect ophthalmoscopy lens is so designed that while in its telecentric position with respect to the eye as shown in FIG. 3, it refracts the emerging homocentric parallel bundles of light rays surrounding each chief ray such that it forms a substantially flat, astigmatism free undistorted aerial image of the fundus of the eye in the anterior focal plane of the lens. FIG. 3 illustrates the second design feature.

Figure 4:
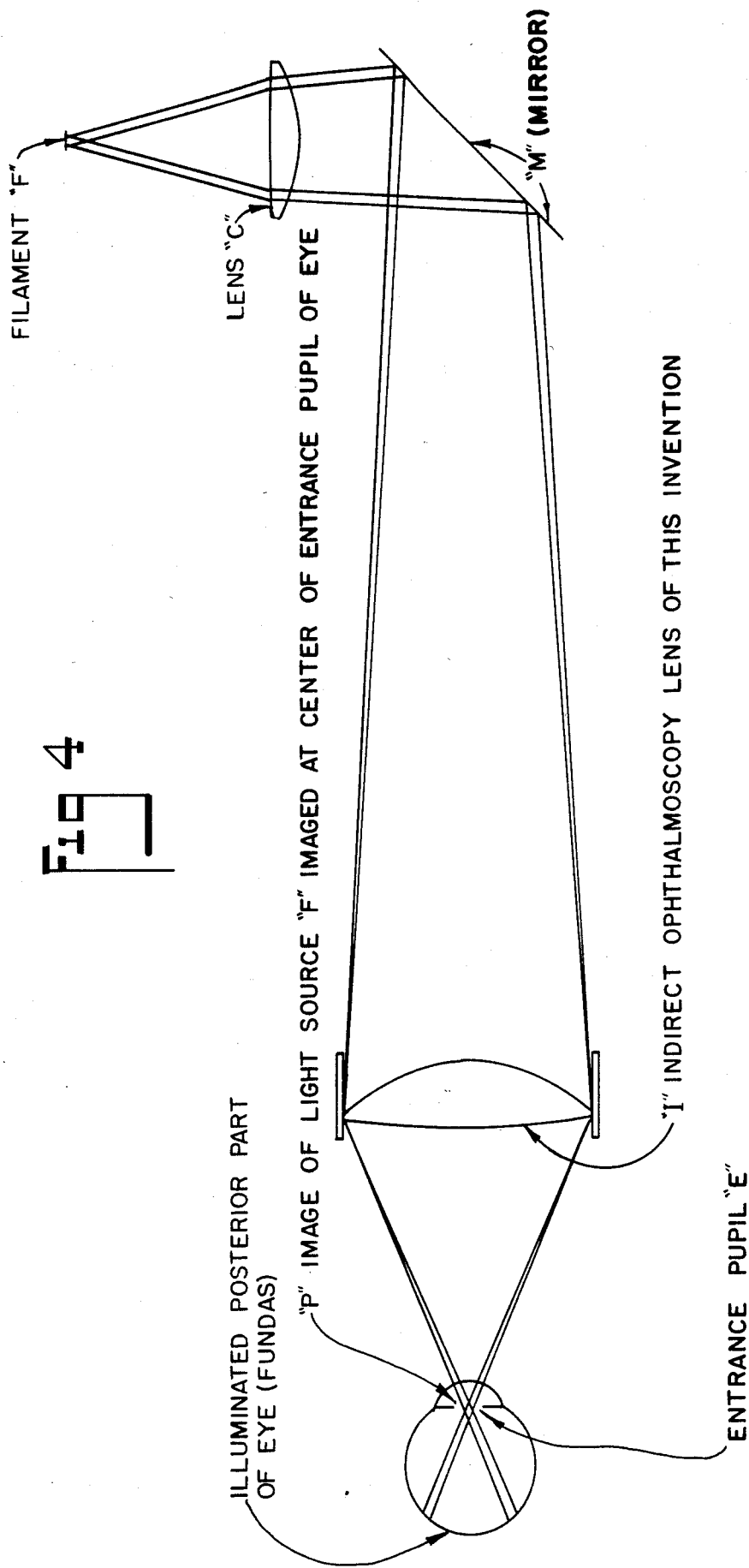
FIG. 4 is a schematic illustration of an ophthalmoscope illuminating system showing the diverging rays from the ophthalmoscope mirror and their coincidence upon a lens of this invention and the refraction of these rays to converge them to an image of the source at the center of the entrance pupil of the eye to illuminate the interior posterior part of the eye.

In order to utilize such a telecentric system as illustrated in FIGS. 2 and 3, both the light source and the observing system of the ophthalmoscope would have to be at an infinite distince from the observed eye. As used in practice, both the light source and the observing system of the ophthalmoscope are relatively close to the observed eye with the light rays diverging from a virtual source toward the indirect ophthalmoscopy lens. The image of the virtual light source as formed by the indirect ophthalmoscopy lens is consequently slightly farther from the lens than the secondary focus of the lens. Consequently the lens must be moved forward a small amount in order that the image of the source be formed at the center of the entrance pupil of the eye. FIG. 4 illustrates light rays originating from a small filament F within the ophthalmoscope and after refraction by lens C, being reflected as a diverging bundle of light rays from mirror M toward the indirect ophthalmoscopy lens I of this invention.

Figure 5:
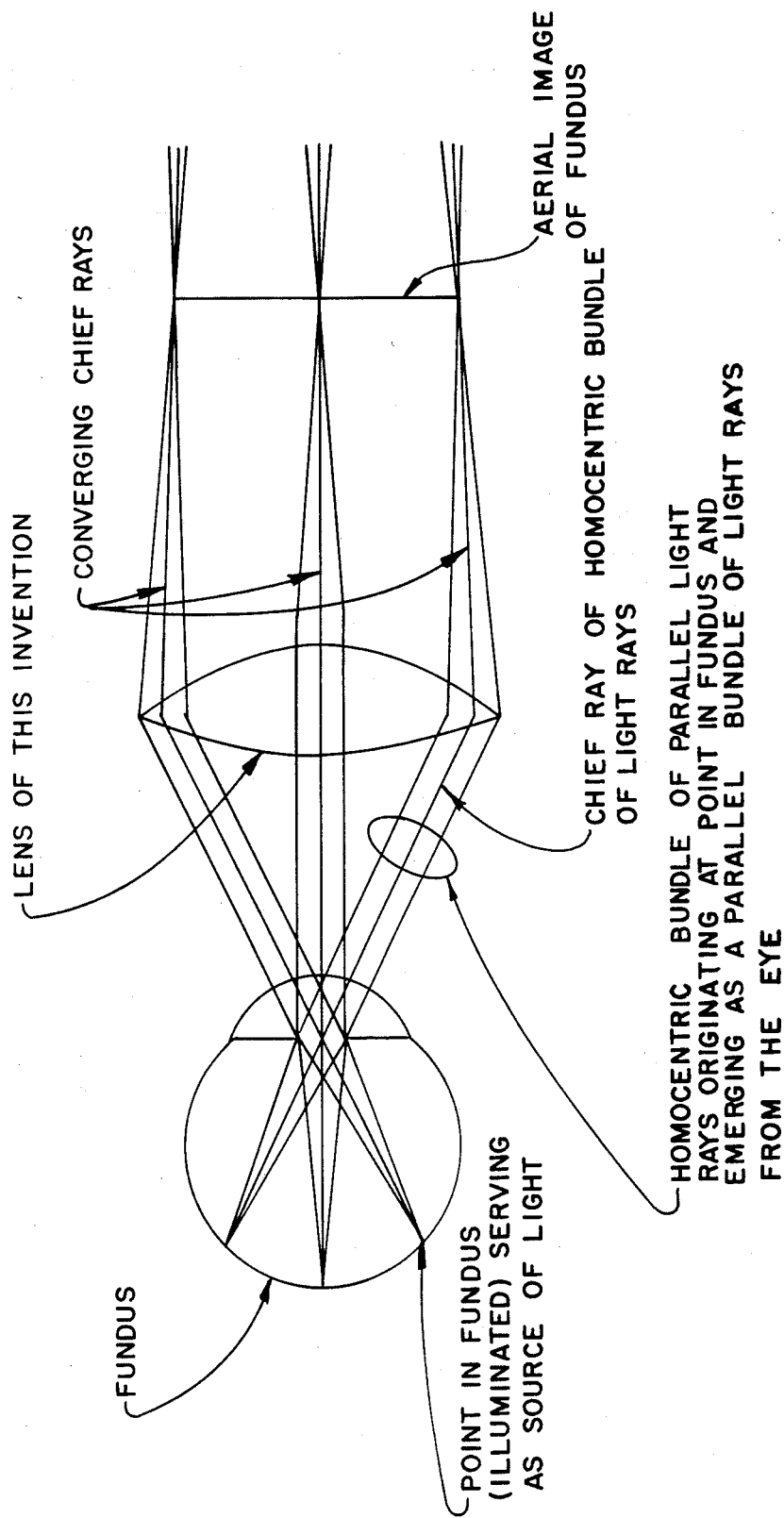
FIG. 5 is a schematic illustration of the formation of an aerial image of the fundus of the eye by the lens of this invention.
Figure 6:
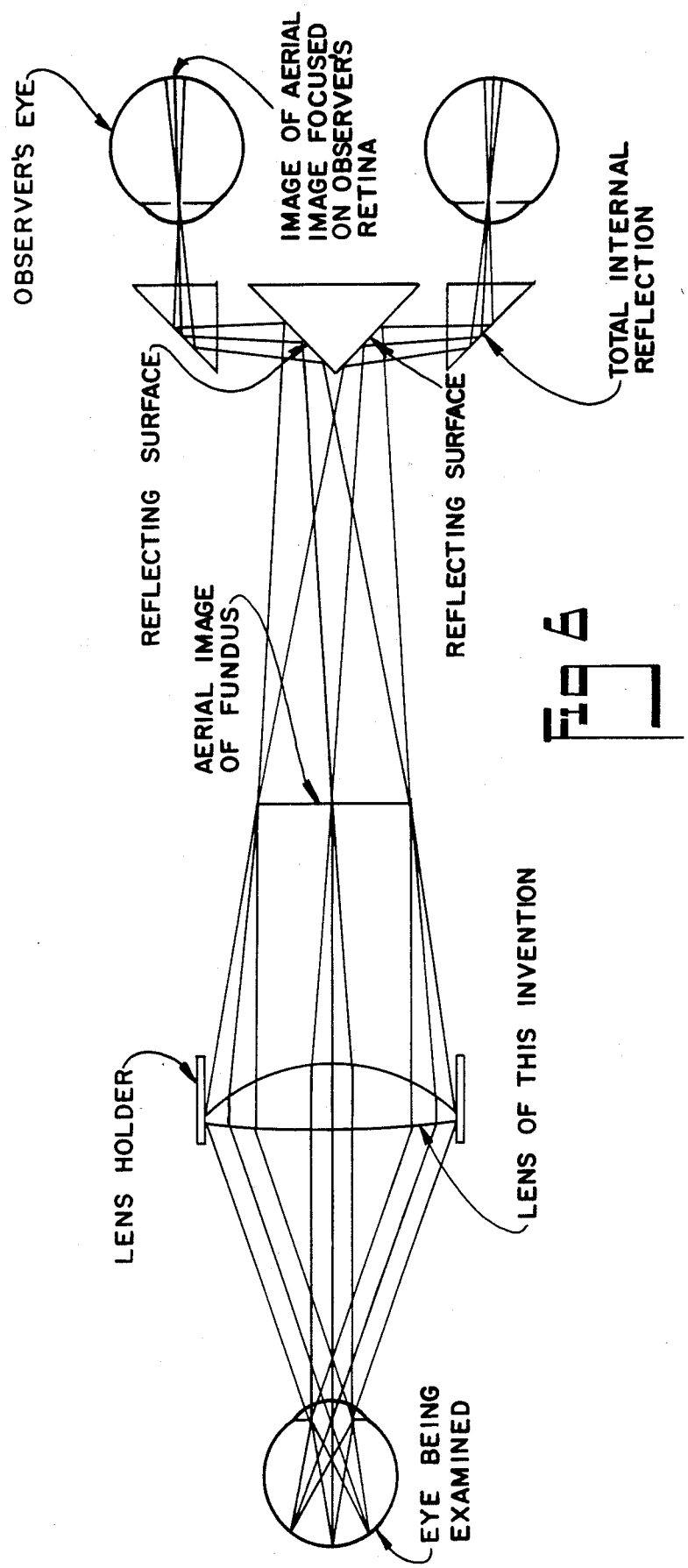
FIG. 6 is a schematic illustration of an ophthalmoscope observing system for observation of the aerial image produced by the lens of this invention showing how said image can be viewed binocularly and stereoscopically.

FIG. 5 illustrates image formation by the indirect ophthalmoscopy lens, the image of the fundus being substantially flat, undistorted and free of astigmatism and formed in the anterior focal plane of the indirect ophthalmoscopy lens, with the chief rays of bundles of light rays emerging from the lens being convergent. FIG. 6 illustrates the optical principals of the observing system of the binocular indirect ophthalmoscope wherein each bundle of light rays proceeding from the aerial image of the fundus toward the ophthalmoscope is divided by a central mirror system to proceed toward right and left prisms which in turn direct the light rays toward the observer's eyes. The departure of indirect opthalmoscopy lens from the idealized telecentric mode wherein the chief rays from the aerial image proceed toward infinity has been taken into account in the design of the novel lens of this invention.

In my research on the lens of this invention, lens design parameters have been determined for a large number of lenses designed with both surfaces convex conoids with a wide range of apical dioptric powers for each of the two surfaces and a wide range of eccentricities for each of the two surfaces of the lens. The optical material considered in this research consisted primarily of ophthalmic drown glass of index of refraction 1.523 and secondarily of ophthalmic plastic of index of refraction 1.498. Glass is preferred because of its resistance to scratching and because it can be multicoated to increase light transmission to better than 99% and thereby reduce len surface reflection. My research also includes lenses made of transparent glass of various colors including white or clear which transmits the entire visible spectrum; yellow which transmits light in the green-yellow-orange-red portion of the visible spectrum; orange-red which transmits light in the orange-red portion of the visible spectrum; green which transmits light in the green portion of the visible spectrum; and blue which transmits light in the violet-blue and green-yellow portions of the visible spectrum.

I have determined in my research that the design of the lens of this invention has the following identified relationships between its various parameters.

The lens material is a homogenous transparent optical material formed of either glass or plastic and having two positive or convex aspheric surfaces of revolution on opposite sides thereof, each having its own axis and wherein the two axes coincide, and which lens is intended to be supported before a patient's eye at a distance that is substantially equal to the secondary focal distance of the lens and with the optical axis of the lens passing through the center of the entrance pupil of the patient's eye. One of the aspheric surfaces of revolution is defined as the front surface of the lens and it faces the examiner, and the other aspheric surface of revolution is defined as the back surface of the lens and faces the eye being examined.

The nominal dioptric power of the lens is defined as the sum of the dioptric power of each of the two lens surfaces at its apex and which nominal dioptric power may vary within the range of approximately 15 to 50 diopters. The dioptric power at the apex of the front surface may vary within the range of approximately 10 to 33.333 diopters and the dioptric power of the back surface may vary within the range of 5 to 16.666 diopters.

As previously indicated, this is the preferred range whereas useful nominal dioptric powers may encompass a range of approximately 10 to 55 diopters. Further, for any lens of this invention the selected dioptric power of the front surface at its apex is approximately twice the dioptric power of the back surface at its apex.

The eccentricity of the front surface may be selected to be any value within the range of 0.80 to 1.45.

The eccentricity of the back surface may lie within the range of 0.50 to 3.80, and for a given selected eccentricity for the front surface within said range the eccentricity of the back surface is so selected as to provide an aerial image of the fundus of the examined eye which least departs from a substantiallY flat astigmatism free image of negligible distortion of the fundus of the eye and which enables clear observation of the full extent of the aerial image of the fundus of the eye by the examiner.

In using the lens of the present invention, it is used in conjunction with a suitable eye illuminating and observing system such as the system illustrated schematically in FIGS. 4 and 6.

In the system, the lens of this invention is held by the examiner in spaced relation in front of the examined eye at a distance substantially equal to the secondary focal distance of the lens, and with the optical axis of the lens lying in the plane which contains the entrance pupil of the observed eye as well as those of the observer, and with the optical axis of the lens lying in said plane and passing through the center of the entrance pupil of the observed eye and passing midway between the entrance pupils of the observer's eyes.

In this system, the lens of the present invention thus produces an aerial image of the fundus of the examined eye that is substantially flat, and substantially free of astigmatism and distortion, thus enabling clear observation by the examiner of the aerial image of the fundus of the examined eye.

I claim:

1. An indirect ophthalmoscopy lens for use in examining a patient's eye comprising a homogeneous transparent optical material having two aspheric surfaces of revolution of conoid type on opposite sides thereof and means for holding said lens to enable the same to be supported in the hand of the examiner before a pateint's eye at a distance substantially equal to the secondary focal distance of the lens with the optical axis of the lens passing through the center of the entrance pupil of the patient's eye, one of the aspheric surfaces of revolution being defined as the front surface which faces the examiner and the other aspheric surface of revolution being defined as the back surface which faces the eye being examined, and wherein the nominal dioptric power of the lens is defined as the sum of the dioptric powers of each of the two surfaces at its apex and which nominal dioptric power is within the range of approximately 10–55 diopters, and wherein the dioptric power at the apex of the front surface is within the range of approximately 6.666 to 36.666 diopters and wherein the dioptric power at the apex of the back surface is selected to be within the range of approximately 3.333 to 18.333 diopters, and wherein for any lens the selected dioptric power of the front surface at its apex is approximately twice the dioptric power of the back surface at its apex, and wherein the eccentricity of the front surface is in the range of 0.80 to 1.45 and the eccentricity of the back surface is in the range of 0.50 3.80, and wherein for a given selected eccentricity for the front suface within said range the eccentricity of the back surface is so selected as to provide an aerial image of the fundus of the examined eye which least departs from a substantially flat astigmatism free image of said fundus and which enables clear observation of the full extent of the extent of the aerial image of the fundus of the eye by the examiner.

2. A lens as in claim 1 in which the homogeneous transparent optical material is glass.

3. A lens as in claim 1 in which the homogeneous transparent optical material is plastic.

4. A lens as in claim 1 of orange-red color in which the spectral transmission of the homogeneous transparent optical material is high and limited almost entirely to the orange-red portion of the visible spectrum.

5. A lens as in claim 1 of green color in which the spectral transmission of the homogeneous transparent optical material is high and limited almost entirely to the green portion of the visible spectrum.

6. A lens as in claim 1 of yellow color in which the spectral transmission of the homogeneous optical material is high and limited almost entirely to the green-yellow-orange-red portion of the visible spectrum.

7. A lens as in claim 1 of blue color in which the spectral transmission of the homogeneous transparent optical material is high and limited almost entirely to the violet-blue and green-yellow portions of the visible spectrum.

8. A lens as in claim 1 in which the homogeneous transparent optical material is fully transparent for the entire visible spectrum.

* * * * *